United States Patent
Ueda et al.

(10) Patent No.: US 7,829,080 B2
(45) Date of Patent: Nov. 9, 2010

(54) STABILIZATION METHOD OF REDUCED COENZYME $Q_{10}$

(75) Inventors: Takahiro Ueda, Kobe (JP); Shiro Kitamura, Akashi (JP); Hiroshi Kubo, Kobe (JP); Kazunori Hosoe, Takasago (JP)

(73) Assignee: Kaneka Corporation, Osaka-shi (JP)

( * ) Notice: Subject to any disclaimer, the term of this patent is extended or adjusted under 35 U.S.C. 154(b) by 0 days.

(21) Appl. No.: 11/741,290

(22) Filed: Apr. 27, 2007

(65) Prior Publication Data

US 2007/0258966 A1  Nov. 8, 2007

(30) Foreign Application Priority Data

Apr. 28, 2006 (JP) .............................. 2006-126897

(51) Int. Cl.
  *A61K 9/64* (2006.01)
  *A61K 38/43* (2006.01)
  *A61K 38/54* (2006.01)

(52) U.S. Cl. ...................... 424/94.1; 424/451; 424/455; 424/456

(58) Field of Classification Search ........................ None
  See application file for complete search history.

(56) References Cited

U.S. PATENT DOCUMENTS 6,878,514 B1 * 4/2005 Morre et al. .................... 435/4

2004/0214301 A1  10/2004 Ueda et al.
2004/0215040 A1  10/2004 Ueda et al.
2005/0008630 A1 *  1/2005 Ueda et al. ................. 424/94.1

FOREIGN PATENT DOCUMENTS

JP    10-109933 A    4/1998
WO   WO 01/52822 A1   7/2001

OTHER PUBLICATIONS

Wakabayashi et al. (1994) Biol. Pharm. Bull. 17(8): 997-1002.*
Lekli et al. (2008) J. Agric. Food chem. 56: 5331-5337.*
Selvam et al., *Nutrition Research*, 13: 667-676 (1993).
Matsura et al., *Biochimica et Biophysica Acta*, 1127: 277-283 (1992).

* cited by examiner

*Primary Examiner*—Lisa J Hobbs
(74) *Attorney, Agent, or Firm*—Leydig, Voit & Mayer, Ltd.

(57) ABSTRACT

The present invention provides a method for stabilizing reduced coenzyme $Q_{10}$, which is useful as a food, nutritional product, nutritional supplement, animal drug, drink, feed, cosmetic, pharmaceutical product, therapeutic drug, prophylactic drug and the like. The present invention also provides a method of producing a reduced coenzyme $Q_{10}$-containing composition which includes the co-presence of reduced coenzyme $Q_{10}$ and reduced coenzyme $Q_9$ and/or reduced coenzyme $Q_{11}$.

18 Claims, 2 Drawing Sheets

Total coenzyme Q in rat plasma

Total coenzyme $Q_{10}$ in rat plasma

STABILIZATION METHOD OF REDUCED COENZYME $Q_{10}$

BACKGROUND OF THE INVENTION

It is known that reduced coenzyme $Q_{10}$ can be obtained, for example, by a method comprising producing coenzyme $Q_{10}$ by a conventionally known method such as synthesis, fermentation, extraction from a naturally occurring substance and the like, and concentrating a reduced coenzyme $Q_{10}$ fraction in an eluate from chromatography and the like (see JP-A-10-109933). In this case, oxidized coenzyme $Q_{10}$ contained in the above-mentioned reduced coenzyme $Q_{10}$ can be reduced with a general reducing agent such as sodium borohydride, sodium dithionite (sodium hydrosulfite) and the like, and concentrated by chromatography, and that the reduced coenzyme $Q_{10}$ can also be obtained by a method comprising reacting existing highly pure coenzyme $Q_{10}$ with the above-mentioned reducing agent.

In addition, production methods for conveniently obtaining reduced coenzyme $Q_{10}$ are also disclosed (e.g., WO 03/06408, WO 03/06409 and WO 03/32967).

However, reduced coenzyme $Q_{10}$ is easily oxidized by molecular oxygen into oxidized coenzyme $Q_{10}$, and therefore, stabilization of reduced coenzyme $Q_{10}$ is an important issue when it is processed into a food, food with nutrient function claims, food for specified health use, nutritional product, nutritional supplement, animal drug, drink, feed, pet food, cosmetic, pharmaceutical product, therapeutic drug, prophylactic drug and the like, or a material or composition therefor, or preserved after processing and the like. Complete removal or blocking of oxygen during the above-mentioned processing and preservation is extremely difficult, and remaining or admixed oxygen particularly during heating for processing and long-term preservation exerts a markedly adverse effect. The above-mentioned oxidation is directly related to quality problems such as the by-product oxidized coenzyme $Q_{10}$.

As mentioned above, stabilization of reduced coenzyme $Q_{10}$ (protection of oxidation) is a highly important object. However, since reduced coenzyme $Q_{10}$ is not commercially available to date, the study of methods and compositions for stable retention of reduced coenzyme $Q_{10}$ has not been undertaken very much.

As a conventionally-known method for stably retaining reduced coenzyme $Q_{10}$, a method including addition of a reducing agent is known. However, some of the reducing agents used therefor are not suitable for food and pharmaceutical agents. For example, WO 01/52822, which discloses a composition concurrently containing a reducing agent and a production method thereof, also discloses (1) a composition comprising reduced coenzyme $Q_{10}$; a reducing agent in an amount effective for eliminating oxidation of reduced coenzyme $Q_{10}$ into oxidized coenzyme $Q_{10}$; a surfactant, vegetable oil or a mixture thereof in an amount effective for dissolving the above-mentioned reduced coenzyme $Q_{10}$ and the above-mentioned reducing agent; and a solvent as necessary, (2) a composition for oral administration wherein the above-mentioned composition is prepared into a gelatin capsule or a tablet, and (3) a method of preparing the above-mentioned composition containing reduced coenzyme $Q_{10}$ in situ using oxidized coenzyme $Q_{10}$ and a reducing agent. However, no detailed description relating to the quality, stabilizing effect and the like of the reduced coenzyme $Q_{10}$ contained in the composition is provided, and the expected level of stabilization is not clear.

In addition, the above-mentioned composition and preparation method thereof are highly complicated and complex since plural roles are conferred to the composition (i.e., firstly, a role as a reaction site for reducing oxidized coenzyme $Q_{10}$ to reduced coenzyme $Q_{10}$, and secondly, a role of stably retaining reduced coenzyme $Q_{10}$). Moreover, the above-mentioned composition and a preparation method thereof are not entirely safe because the reaction mixture is used as it is. In other words, ascorbic acids to be used as reducing agents are oxidized to produce a considerable amount of dehydroascorbic acids, and the dehydroascorbic acids get mixed in with the above-mentioned composition, posing a problem. Dehydroascorbic acids and oxalic acid produced by decomposition from dehydroascorbic acids are highly noxious, unlike ascorbic acids. For example, an increased amount of lipid peroxide and a decreased amount of antioxidants in the liver and kidney, and an increased amount of oxalic acid in the kidney have been reported, and side effects such as decreased resistance to oxidation stress, easy onset of ureteral lithiasis (Nutrition Research Vol. 13, page 667-676, 1993) and the like are feared.

SUMMARY OF THE INVENTION

The present invention aims at providing a convenient and preferable method and a composition for stably retaining reduced coenzyme $Q_{10}$ by protection against oxidation while maintaining high safety, during processing into a food, food with nutrient function claims, food for specified health use, nutritional product, nutritional supplement, animal drug, drink, feed, pet food, cosmetic, pharmaceutical product, therapeutic drug, prophylactic drug containing reduced coenzyme $Q_{10}$ and the like, or a material or composition therefor, and/or preservation after processing and the like.

The present inventors have conducted intensive studies in an attempt to solve the above-mentioned problems and found that reduced coenzyme $Q_{10}$ can be stabilized by the co-presence of reduced coenzyme $Q_9$ and/or reduced coenzyme $Q_{11}$, which are analogs of reduced coenzyme $Q_{10}$.

That is, they have found that reduced coenzyme $Q_{10}$ can be stably retained by protecting the reduced coenzyme $Q_{10}$ from oxidation by the co-presence of reduced coenzyme $Q_9$ (not less than 0.6 wt % relative to reduced coenzyme $Q_{10}$) and/or reduced coenzyme $Q_{11}$, even when a reducing agent is not used as a necessary component to be added, which resulted in the completion of the present invention.

Accordingly, the present invention provides the following embodiments.

[1] A method for stabilizing reduced coenzyme $Q_{10}$, which method comprises preparing a reduced coenzyme $Q_{10}$-containing composition comprising reduced coenzyme $Q_{10}$ and one or both of (a) and (b):

(a) not less than 0.6 wt % of reduced coenzyme $Q_9$ relative to reduced coenzyme $Q_{10}$, and (b) reduced coenzyme $Q_{11}$, thereby stabilizing reduced coenzyme $Q_{10}$.

[2] The method of [1], wherein the amount of the reduced coenzyme $Q_9$ is not less than 1 wt % relative to reduced coenzyme $Q_{10}$.

[3] The method of [1], wherein the reduced coenzyme $Q_{10}$-containing composition comprises not less than 0.6 wt % of reduced coenzyme $Q_9$ relative to reduced coenzyme $Q_{10}$.

[4] The method of [1]-[3], wherein the method comprises
preparing one or both of (a) the reduced coenzyme $Q_9$ and (b) the reduced coenzyme $Q_{11}$, and then
adding one or both of (a) the reduced coenzyme $Q_9$ and (b) the reduced coenzyme $Q_{11}$ to the reduced coenzyme $Q_{10}$ to prepare the reduced coenzyme $Q_{10}$-containing composition.

[5] The method of [1]-[3], wherein the method comprises
providing a composition comprising oxidized coenzyme $Q_{10}$ and one or both of oxidized coenzyme $Q_9$ and oxidized coenzyme $Q_{11}$, and then
reducing oxidized coenzyme $Q_{10}$ and reducing one or both of oxidized coenzyme $Q_9$ and oxidized coenzyme $Q_{11}$ to prepare the reduced coenzyme $Q_{10}$-containing composition.

[6] The method of [1]-[5], wherein the reduced coenzyme $Q_{10}$-containing composition is prepared under a deoxygenation atmosphere.

[7] A reduced coenzyme $Q_{10}$-containing composition comprising reduced coenzyme $Q_{10}$ and one or both of (a) and (b):
(a) not less than 0.6 wt % of reduced coenzyme $Q_9$ relative to reduced coenzyme $Q_{10}$, and
(b) reduced coenzyme $Q_{11}$.

[8] The composition of [7], wherein the amount of the reduced coenzyme $Q_9$ is not less than 1 wt % relative to reduced coenzyme $Q_{10}$.

[9] The composition of [7], wherein the composition comprises not less than 0.6 wt % of reduced coenzyme $Q_9$ relative to reduced coenzyme $Q_{10}$.

[10] The composition of [7]-[9], wherein the reduced coenzyme $Q_{10}$ is in crystalline form.

[11] The composition of [7]-[9], wherein the reduced coenzyme $Q_{10}$ is dissolved or suspended in a solvent.

[12] The composition of [7]-[9], wherein the reduced coenzyme $Q_{10}$ is a melt.

[13] The composition of [7]-[12], which further comprises a pharmaceutically acceptable carrier.

[14] The composition of [7]-[13], which is in a form suitable for administration to a mammal and comprises reduced coenzyme $Q_{10}$ as an active ingredient.

[15] The composition of [7]-[14], which further comprises at least one component selected from the group consisting of an excipient, a disintegrant, a lubricant, a binder, an antioxidant, a coloring agent, an anticoagulant, an absorption promoter, a solubilizing agent for the active ingredient, a stabilizer, an active ingredient other than reduced coenzyme $Q_{10}$, and combinations thereof.

[16] An oral dosage form comprising the composition of [15], which dosage form is a capsule.

[17] The oral dosage form of [16], wherein the capsule is a microcapsule, a soft capsule, or a hard capsule.

[18] A method for producing a reduced coenzyme $Q_{10}$-containing composition, which method comprises
preparing one or both of (a) reduced coenzyme $Q_9$ and (b) reduced coenzyme $Q_{11}$, and then
adding one or both of (a) the reduced coenzyme $Q_9$ and (b) the reduced coenzyme $Q_{11}$ to reduced coenzyme $Q_{10}$ to prepare the reduced coenzyme $Q_{10}$-containing composition,
wherein the composition comprises reduced coenzyme $Q_{10}$ and one or both of (a) not less than 0.6 wt % of reduced coenzyme $Q_9$ relative to reduced coenzyme $Q_{10}$ and (b) reduced coenzyme $Q_{11}$.

[19] The method of [18], wherein the reduced coenzyme $Q_{10}$-containing composition comprises not less than 0.6 wt % of reduced coenzyme $Q_9$ relative to reduced coenzyme $Q_{10}$.

[20] A method for producing a reduced coenzyme $Q_{10}$-containing composition, which method comprises
providing a composition comprising oxidized coenzyme $Q_{10}$ with one or both of oxidized coenzyme $Q_9$ and oxidized coenzyme $Q_{11}$, and then
reducing oxidized coenzyme $Q_{10}$ and reducing one or both of oxidized coenzyme $Q_9$ and oxidized coenzyme $Q_{11}$ to prepare the reduced coenzyme $Q_{10}$-containing composition,
wherein the composition comprises reduced coenzyme $Q_{10}$ and one or both of (a) not less than 0.6 wt % of reduced coenzyme $Q_9$ relative to reduced coenzyme $Q_{10}$ and (b) reduced coenzyme $Q_{11}$.

[21] The method of [20], wherein the reduced coenzyme $Q_{10}$-containing composition comprises not less than 0.6 wt % of reduced coenzyme $Q_9$ relative to reduced coenzyme $Q_{10}$.

DETAILED DESCRIPTION OF THE INVENTION

Figure 1:
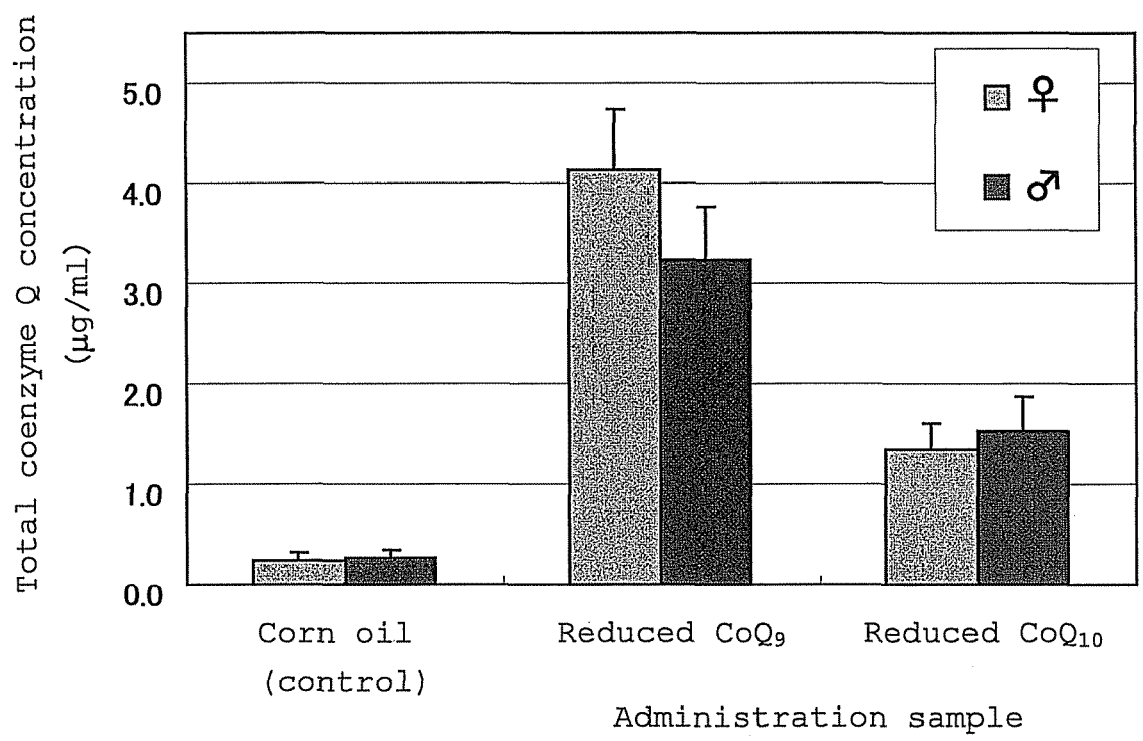
FIG. 1 is a bar graph that sets forth the concentration of the total coenzyme Q (µg/ml) in plasma from male and female rats following administration of (1) corn oil (control), (2) reduced coenzyme $Q_9$, and (3) reduced coenzyme $Q_{10}$ as set forth in Example 3.

According to the present invention, a stabilization method of reduced coenzyme $Q_{10}$ can be provided by a mere co-presence of an analog of reduced coenzyme $Q_{10}$ even when multiple components, particularly a reducing agent, are not used as necessary components to protect the reduced coenzyme $Q_{10}$ from oxidation. Therefore, highly safe reduced coenzyme $Q_{10}$ can be provided, which is free of a noxious substance such as dehydroascorbic acid, oxalic acid and the like produced when ascorbic acid and the like is used as a reducing agent.

Moreover, reduced coenzyme $Q_9$ and reduced coenzyme $Q_{11}$ show the same effect in the body as reduced coenzyme $Q_{10}$. Therefore, when reduced coenzyme $Q_9$ and reduced coenzyme $Q_{11}$ contained in reduced coenzyme $Q_{10}$ are ingested, the effect of the reduced coenzyme $Q_{10}$ is not prevented, and a greater effect of coenzyme Q can be exhibited as compared to a composition containing reduced coenzyme $Q_{10}$ alone, and the like. Furthermore, since the absorbability of reduced coenzyme $Q_9$ in the body is greater than that of reduced coenzyme $Q_{10}$, a composition containing reduced coenzyme $Q_9$ and reduced coenzyme $Q_{10}$ in combination shows higher absorbability in terms of the total amount of coenzyme Q.

The present invention is explained in detail below. In the present specification, the phrase "coenzyme $Q_{10}$," when simply expressed includes the oxidized form, the reduced form, and/or a mixture thereof when they are both present.

In the present invention, reduced coenzyme $Q_{10}$ can contain oxidized coenzyme $Q_{10}$. When oxidized coenzyme $Q_{10}$ is also present, the proportion of reduced coenzyme $Q_{10}$ in the total amount of coenzyme $Q_{10}$ (i.e., the total amount of reduced coenzyme $Q_{10}$ and oxidized coenzyme $Q_{10}$) is not particularly limited. Preferably, the proportion of reduced coenzyme $Q_{10}$ in the total amount of coenzyme $Q_{10}$ is not less than 20 wt % (e.g., not less than 25 wt %, not less than 30 wt %, not less than 35 wt %, not less than 40 wt %, not less than 45 wt %, not less than 50 wt %, not less than 60 wt %, not less than 65 wt %, not less than 70 wt %, not less than 75 wt %, not less than 80 wt %, not less than 85 wt %, not less than 90%, not less than 95%, or not less than 96%). While the upper limit is not particularly limited (i.e., the upper limit can be 100 wt %), typically the upper limit is not more than 99.9 wt % (e.g., not more than 99.5 wt %, or not more than 99.0 wt %).

Reduced coenzyme $Q_{10}$ can be obtained by various methods as mentioned above. For example, reduced coenzyme $Q_{10}$ having a high proportion of reduced coenzyme $Q_{10}$ relative to the total amount of coenzyme $Q_{10}$ can be efficiently obtained by the method described in WO 03/06408.

The stabilization method of the reduced coenzyme $Q_{10}$ of the present invention (hereinafter to be also referred to as the stabilization method of the present invention) is a method characterized by the co-presence of (a) not less than 0.6 wt % of reduced coenzyme $Q_9$ relative to reduced coenzyme $Q_{10}$, and/or (b) reduced coenzyme $Q_{11}$, which suppresses oxidation of reduced coenzyme $Q_{10}$ into oxidized coenzyme $Q_{10}$ by molecular oxygen, and stably retains the reduced coenzyme $Q_{10}$.

While the amount of reduced coenzyme $Q_9$ and/or reduced coenzyme $Q_{11}$ contained in reduced coenzyme $Q_{10}$ is not particularly limited, the amount of the reduced coenzyme $Q_9$ is generally not less than about 0.6 wt %, preferably not less than about 1 wt %, more preferably not less than about 1.5 wt %, more preferably not less than about 2 wt %, and most preferably not less than about 3 wt %, relative to reduced coenzyme $Q_{10}$.

The amount of reduced coenzyme $Q_{11}$ is generally not less than about 0.1 wt %, preferably not less than about 0.5 wt %, and more preferably not less than about 1 wt %, relative to reduced coenzyme $Q_{10}$.

While the upper limit of reduced coenzyme $Q_9$ and/or reduced coenzyme $Q_{11}$ contained in reduced coenzyme $Q_{10}$ is not particularly limited, it is generally not more than about 99 wt % (e.g., not more than about 90 wt %, not more than about 80 wt %, not more than about 70 wt %, not more than about 60 wt %, not more than about 50 wt %, or not more than about 40 wt %). Both reduced coenzyme $Q_9$ and reduced coenzyme $Q_{10}$ can be present with reduced coenzyme $Q_{10}$.

In the stabilization method of the present invention, the aforementioned (a) and/or (b) can be separately prepared by any suitable technique. For example, the separate preparation can be preparation by extraction and purification from a naturally occurring substance, reduction of oxidized coenzyme $Q_9$ and oxidized coenzyme $Q_{11}$ according to the aforementioned method described in WO 03/06408, or coupling reaction of isoprenyl side chain with 2-methyl-5,6-dimethoxy-1,4-benzohydroquinone and the like. The reduced coenzyme $Q_{10}$ can also be stabilized by adding (a) and/or (b) obtained by such preparation to reduced coenzyme $Q_{10}$.

The stabilization method of the present invention also includes the co-presence of reduced coenzyme $Q_{10}$ and (a) and/or (b) by the reduction of oxidized coenzyme $Q_{10}$ containing oxidized coenzyme $Q_9$ and/or oxidized coenzyme $Q_{11}$.

The method of reducing oxidized coenzyme $Q_{10}$ containing oxidized coenzyme $Q_9$ and/or oxidized coenzyme $Q_{11}$ can be performed according to the method described in WO 03/06408 and the like.

The reduced coenzyme $Q_{10}$-containing composition of the present invention (hereinafter to be also referred to as the composition of the present invention) is a composition characterized by the co-presence of (a) not less than 0.6 wt % of reduced coenzyme $Q_9$ relative to reduced coenzyme $Q_{10}$, and/or (b) reduced coenzyme $Q_{11}$.

Preferable amounts of reduced coenzyme $Q_9$ and/or reduced coenzyme $Q_{11}$ to be contained in reduced coenzyme $Q_{10}$ are as mentioned above.

The composition of the present invention can be obtained by adding separately prepared reduced coenzyme $Q_9$ and/or reduced coenzyme $Q_{11}$ to reduced coenzyme $Q_{10}$, or reducing oxidized coenzyme $Q_{10}$ containing oxidized coenzyme $Q_9$ and/or oxidized coenzyme $Q_{11}$.

The production method of the reduced coenzyme $Q_{10}$-containing composition of the present invention (hereinafter to be also referred to as the production method of the present invention) is a production method of a reduced coenzyme $Q_{10}$-containing composition comprising the aforementioned (a) and/or (b) in combination, which includes separately preparing and adding (a) and/or (b).

The production method of reduced coenzyme $Q_{10}$ containing reduced coenzyme $Q_9$ and/or reduced coenzyme $Q_{11}$ is not particularly limited. The step of separately preparing and adding (a) and/or (b) can be a step for adding (a) and/or (b) separately prepared as mentioned above. The preparation and addition can be performed by any suitable method known in the art.

The production method of the present invention includes a step of reducing oxidized coenzyme $Q_{10}$ containing of oxidized coenzyme $Q_9$ (not less than 0.6 wt % relative to oxidized coenzyme $Q_{10}$) and/or oxidized coenzyme $Q_{11}$. By this step, reduced coenzyme $Q_{10}$-containing composition containing (a) and/or (b) in combination (and in the previously mentioned amounts) can be finally obtained.

The method (step) of reducing oxidized coenzyme $Q_{10}$ containing oxidized coenzyme $Q_9$ and/or oxidized coenzyme $Q_{11}$, and the method (step) of adding reduced coenzyme $Q_9$ and/or reduced coenzyme $Q_{11}$ prepared separately, can be employed in combination.

The form of the reduced coenzyme $Q_{10}$-containing composition containing reduced coenzyme $Q_9$ and/or reduced coenzyme $Q_{11}$ in combination of the present invention is not particularly limited, and can be a crystal; dissolved or suspended in a solvent; a melt maintained at not less than the melting point; or in a form for administration to mammals such as an agent for oral administration, external preparation and the like.

In the present invention, the form of contact between reduced coenzyme $Q_{10}$ and reduced coenzyme $Q_9$ and/or reduced coenzyme $Q_{11}$ is not particularly limited. For example, reduced coenzyme $Q_{10}$ and reduced coenzyme $Q_9$ and/or reduced coenzyme $Q_{11}$ can be present as crystals, or dissolved and/or suspended in any solvent. Also, reduced coenzyme $Q_9$ and/or reduced coenzyme $Q_{11}$ can be dissolved in a melted solution of reduced coenzyme $Q_{10}$.

As the solvent usable in the present invention is not particularly limited, and hydrocarbons, fatty acid esters, ethers, alcohols, fatty acids, ketones, nitrogen compounds (including nitriles and amides), sulfur compounds, fats and oils, water and the like can be used. These solvents can be a mixture of any two or more kinds of solvents.

The suitable hydrocarbons are not particularly limited. For example, aliphatic hydrocarbon, aromatic hydrocarbon, halogenated hydrocarbon and the like can be used. Aliphatic hydrocarbon and aromatic hydrocarbon are preferable, and aliphatic hydrocarbon is especially preferable.

Aliphatic hydrocarbons can be cyclic or non-cyclic, saturated or unsaturated, and are not particularly limited. Generally, saturated aliphatic hydrocarbons are preferably used.

Aliphatic hydrocarbons having 3 to 20 carbon atoms, particularly 5 to 12 carbon atoms, especially 5 to 8 carbon atoms, are preferably used. Specific examples include propane, butane, isobutane, pentane, 2-methylbutane, hexane, 2-methylpentane, 2,2-dimethylbutane, 2,3-dimethylbutane, heptane, heptane isomer (e.g., 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane, cyclohexene and the like.

Of these, pentane, 2-methylbutane, hexane, 2-methylpentane, 2,2-dimethylbutane, 2,3-dimethylbutane, heptane, heptane isomer (e.g., 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane, p-menthane and the like are preferable, and particularly, pentane, 2-methylbutane, hexane, 2-methylpentane, 2,2-dimethylbutane, 2,3-dimethylbutane, heptane, heptane isomer (e.g., 2-methylhexane, 3-methylhexane, 2,3-dimethylpentane, 2,4-dimethylpentane), octane, 2,2,3-trimethylpentane, isooctane, cyclopentane, methylcyclopentane, cyclohexane, methylcyclohexane, ethylcyclohexane and the like are preferable.

Pentanes having 5 carbon atoms (e.g., pentane etc.), hexanes having 6 carbon atoms (e.g., hexane, cyclohexane etc.), heptanes having 7 carbon atoms (e.g., heptane, methylcyclohexane etc.) and the like, as well as mixtures thereof (e.g., two or more heptanes) are preferably used. Heptanes (e.g., heptane, methylcyclohexane etc.) are most preferable, and heptane is especially preferable.

While aromatic hydrocarbons are not particularly limited, normally, an aromatic hydrocarbon having 6 to 20 carbon atoms, particularly 6 to 12 carbon atoms, especially 7 to 10 carbon atoms, is preferably used. Specific examples include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene and the like.

Of these, toluene, xylene, o-xylene, m-xylene, p-xylene, ethylbenzene, cumene, mesitylene, tetralin, butylbenzene, p-cymene, cyclohexylbenzene, diethylbenzene, pentylbenzene and the like are preferable, and particularly, toluene, xylene, o-xylene, m-xylene, p-xylene, cumene, tetralin and the like are preferable. Cumene is most preferable.

Halogenated hydrocarbons can be cyclic or non-cyclic, saturated or unsaturated, and are not particularly limited. In general, a non-cyclic halogenated hydrocarbon is preferably used. Halogenated hydrocarbon having 1 to 6 carbon atoms, particularly 1 to 4 carbon atoms, especially 1 or 2 carbon atoms, are preferably used. Chlorinated hydrocarbon and fluorinated hydrocarbon are preferable, and chlorinated hydrocarbon is particularly preferable. Specific examples include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane and the like.

Of these, dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene, 1,1,1,2-tetrafluoroethane and the like preferably, particularly, dichloromethane, chloroform, 1,2-dichloroethylene, trichloroethylene, chlorobenzene, 1,1,1,2-tetrafluoroethane and the like are preferable.

Fatty acid esters are not particularly limited. For example, propionic acid ester, acetic acid ester, formic acid ester and the like can be used. Acetic acid ester and formic acid ester are preferable, and acetic acid ester is particularly preferable.

While the ester group is not particularly limited, alkyl ester or aralkyl ester having 1 to 8 carbon atoms, preferably aralkyl ester having 1 to 6 carbon atoms, more preferably aralkyl ester having 1 to 4 carbon atoms is preferably used.

Specific examples of propionic acid ester include methyl propionate, ethyl propionate, butyl propionate and isopentyl propionate.

Specific examples of acetic acid ester include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate and the like. Of these, methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate and the like are preferable. Methyl acetate, ethyl acetate, propyl acetate, isopropyl acetate, butyl acetate, isobutyl acetate and the like are more preferable, and ethyl acetate is particularly preferable.

Examples of formic acid ester include methyl formate, ethyl formate, propyl formate, isopropyl formate, butyl formate, isobutyl formate, sec-butyl formate, pentyl formate and the like.

Of these, methyl formate, ethyl formate, propyl formate, butyl formate, isobutyl formate, pentyl formate and the like are preferable. Ethyl formate is more preferable.

Ethers can be cyclic or non-cyclic, saturated or unsaturated, and are not particularly limited. In general, saturated ethers are preferably used.

Ether having 3 to 20 carbon atoms, particularly ether having 4 to 12 carbon atoms, especially ether having 4 to 8 carbon atoms, is preferably used. Specific examples include diethyl ether, methyl tert-butyl ether, dipropyl ether, diisopropyl ether, dibutyl ether, dihexyl ether, ethylvinyl ether, butylvinyl ether, anisole, phenetol, butylphenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol dibutyl ether and the like.

Of these, diethyl ether, methyl tert-butyl ether, dipropyl ether, diisopropyl ether, dibutyl ether, dihexyl ether, anisole, phenetol, butylphenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether and the like are preferable, and particularly, diethyl ether, methyl tert-butyl ether, anisole, dioxane, tetrahydrofuran, ethylene glycol monomethyl ether, ethylene glycol monoethyl ether and the like are preferable.

Diethyl ether, methyl tert-butyl ether, anisole, dioxane, tetrahydrofuran and the like are most preferable, and dioxane and tetrahydrofuran are particularly preferable.

Nitriles can be cyclic or non-cyclic, saturated or unsaturated, and are not particularly limited. In general, saturated nitrites are preferably used.

A nitrile having 2 to 20 carbon atoms, particularly a nitrile having 2 to 12 carbon atoms, especially nitrile having 2 to 8 carbon atoms, is preferably used. Specific examples include acetonitrile, propionitrile, malononitrile, butyronitrile, isobutyronitrile, succinonitrile, valeronitrile, glutaronitrile, hexanenitrile, heptyl cyamide, octyl cyamide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphtonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzyl cyamide, cyclopropanecarbonitrile, cyclohexanecarbonitrile, cycloheptanecarbonitrile, phenylcyclohexanecarbonitrile, tolylcyclohexanecarbonitrile and the like.

Alcohols can be cyclic or non-cyclic, saturated or unsaturated, and are not particularly limited. In general, a saturated alcohol is preferably used.

Normally, alcohol having 1 to 20 carbon atoms, particularly alcohol having 1 to 12 carbon atoms, especially alcohol having 1 to 6 carbon atoms, particularly monovalent alcohol having 1 to 5 carbon atoms, divalent alcohol having 2 to carbon atoms or trivalent alcohol having 3 carbon atoms is preferably used. Specific examples of these alcohols include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, 2-methoxyethanol, 2-ethoxyethanol, 2-(methoxymethoxy)ethanol, 2-isoproxy ethanol, 2-butoxy ethanol, 2-(isopentyloxy)ethanol, 2-(hexyloxy)ethanol, furfuryl alcohol, diethylene glycol monomethyl ether, diethylene glycol monoethyl ether, diethylene glycol monobutyl ether, triethylene glycol monomethyl ether, 1-methoxy-2-propanol, 1-ethoxy-2-propanol, dipropylene glycol monomethyl ether, dipropylene glycol monoethyl ether, tripropylene glycol monomethyl ether, 1,2-ethanediol, 1,2-propanediol, 1,3-propanediol, 1,2-butanediol, 1,3-butanediol, 1,4-butanediol, 2,3-butanediol, 1,5-pentanediol, 2-butene-1,4-diol, 2-methyl-2,4-pentanediol, 2-ethyl-1,3-hexanediol, diethylene glycol, triethylene glycol, tetraethylene glycol, polyethylene glycol, dipropylene glycol, polypropylene glycol, glycerol and the like.

Preferable examples of monovalent alcohol include methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzyl alcohol, cyclohexanol, 1-methylcyclohexanol, 2-methylcyclohexanol, 3-methylcyclohexanol, 4-methylcyclohexanol, 2-methoxyethanol, 2-ethoxyethanol, 2-(methoxymethoxy)ethanol and the like, and particularly, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, cyclohexanol and the like are preferable. Methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol and the like are particularly preferable.

Methanol, ethanol, 1-propanol, 2-propanol, 1-butanol, 2-butanol, isobutyl alcohol, 2-methyl-1-butanol, isopentyl alcohol and the like are most preferable. Methanol, ethanol, 1-propanol and 2-propanol are particularly preferable, and ethanol is especially preferable.

As divalent alcohol, 1,2-ethanediol, 1,2-propanediol, 1,3-propanediol, 2-butene-1,4-diol, 2-methyl-2,4-pentanediol, 2-ethyl-1,3-hexanediol, diethylene glycol, triethylene glycol, tetraethylene glycol, polyethylene glycol, dipropylene glycol, polypropylene glycol and the like are preferable. 1,2-propanediol and polyethylene glycol are most preferable. As a trivalent alcohol, glycerol is preferable.

Ketones are not particularly limited, and a ketone having 3 to 6 carbon atoms is generally preferable.

Specific examples of ketones include acetone, methylethylketone, methylbutylketone, methylisobutylketone and the like. Acetone and methylethylketone are preferable, and acetone is particularly preferable.

Examples of nitrogen compounds include nitromethane, acetonitrile, triethylamine, pyridine, formamide, N-methylformamide, N,N-dimethylformamide, N,N-dimethylacetamide, N-methylpyrrolidone and the like, and acetonitrile is particularly preferable.

Examples of sulfur compounds include dimethyl sulfoxide, sulfolane and the like. Dimethyl sulfoxide is preferable.

Examples of fatty acids include formic acid, acetic acid, propionic acid, oleic acid, linoleic acid, linolenic acid and the like. Formic acid and acetic acid are preferable, and acetic acid is more preferable.

Fats and oils are not particularly limited, and can be natural fats and oils from plants and animals, synthetic fats and oils or processed fats and oils.

Examples of vegetable oil include olive oil, coconut oil, palm oil, palm kernel oil, flaxseed oil, camellia oil, brown rice germ oil, canola oil, rice oil, peanuts oil, corn oil, wheat germ oil, soy bean oil, perilla oil, cottonseed oil, sunflower kerel oil, kapok oil, evening primrose oil, shea butter, sal butter, cacao butter, sesame oil, safflower oil and the like, and examples of animal fats and oils include lard, milk fat, fish oil, beef fat and the like. Furthermore, fats and oils obtained by processing them by fractionation, hydrogenation, transesterification (e.g., hydrogenated oil) and the like also can be used. Medium-chain triglyceride (MCT), partial glyceride of fatty acid, phospholipid and the like can also be used.

Examples of medium-chain triglyceride include triglyceride wherein the fatty acid has 6 to 12 carbon atoms, preferably 8 to 12 carbon atoms. Examples of partial glyceride of fatty acid include monoglyceride and diglycerides wherein the fatty acid has 6 to 18 carbon atoms, preferably 6 to 12 carbon atoms.

Of the above-mentioned fats and oils, vegetable fats and oils, synthetic fats and oils and processed fats and oils are preferable from the aspects of handlability, odor and the like.

Fats and oils are preferably selected in consideration of the price of fats and oils, stability of reduced coenzyme $Q_{10}$, solubility of coenzyme $Q_{10}$ and the like.

For example, olive oil, coconut oil, palm oil, palm kernel oil, canola oil, rice oil, soy bean oil, cottonseed oil, MCT and the like are preferable, olive oil, rice oil, soy bean oil, canola oil, MCT and the like are particularly preferable.

From the aspect of the solubility of coenzyme $Q_{10}$, MCT can be particularly preferably used.

When the composition of the present invention is used for a food or pharmaceutical agent, ethanol, water and fats and oils usable for the food or pharmaceutical agent are preferably used, from among the above-mentioned solvents. The composition of the present invention can contain other appropriate materials, besides the above-mentioned solvent, such as a carrier. That is, the composition can comprise an excipient, disintegrant, lubricant, binder, antioxidant, coloring agent, anticoagulant, absorption promoter, solubilizing agent for the active ingredient, stabilizer, active ingredient other than reduced coenzyme $Q_{10}$, or combinations thereof. The carrier can be a pharmaceutically acceptable carrier.

The above-mentioned excipient is not particularly limited. For example, sucrose, lactose, glucose, cornstarch, mannitol, crystalline cellulose, calcium phosphate, calcium sulfate and the like can be used as an excipient.

The above-mentioned disintegrant is not particularly limited. For example, starch, agar, calcium citrate, calcium carbonate, sodium hydrogencarbonate, dextrin, crystalline cellulose, carboxymethylcellulose, tragacanth and the like can be used as a disintegrant.

While the above-mentioned lubricant is not particularly limited. For example, talc, magnesium stearate, polyethylene glycol, silica, hydrogenated vegetable oil and the like can be used as a lubricant.

The above-mentioned binder is not particularly limited. For example, ethylcellulose, methylcellulose, hydroxypropylmethylcellulose, tragacanth, shellac, gelatin, gum arabic, polyvinylpyrrolidone, polyvinyl alcohol, polyacrylic acid, polymethacrylic acid, sorbitol and the like can be used as a binder.

The above-mentioned antioxidant is not particularly limited. For example, ascorbic acid, tocopherol, vitamin A, β-carotene, sodium hydrogensulfite, sodium thiosulfate, sodium pyrrosulfite, citric acid and the like can be used as an antioxidant.

The above-mentioned coloring agent is not particularly limited. For example, those allowed to be added to pharmaceutical products and food and the like can be used as a coloring agent.

The above-mentioned anticoagulant is not particularly limited. For example, stearic acid, talc, light anhydrous silicic acid, water-containing silicon dioxide and the like can be used as an anticoagulant.

The above-mentioned absorption promoter is not particularly limited. For example, higher alcohols, higher fatty acids, sucrose fatty acid ester, surfactants such as sorbitan fatty acid ester, sorbitan polyoxyethylene fatty acid ester and the like, and the like can be used as an absorption promoter.

The solubilizing agent for the above-mentioned active ingredient is not particularly limited. For example, organic acids such as fumaric acid, succinic acid, malic acid and the like, and the like can be used as a dissolution aid.

The above-mentioned stabilizer is not particularly limited. For example, benzoic acid, sodium benzoate, ethyl parahydroxybenzoate and the like can be used as a stabilizer.

The active ingredient other than the above-mentioned coenzyme $Q_{10}$ can be any other suitable active agent, such as an amino acid, vitamin, mineral, polyphenol, organic acid, saccharides, peptide, protein and the like.

While the amount of the reduced coenzyme $Q_{10}$ contained in the composition of the present invention is not particularly limited, the weight of the reduced coenzyme $Q_{10}$ contained in the whole composition is generally not less than about 0.01 wt %, preferably not less than about 0.1 wt %, more preferably not less than about 1 wt %, particularly preferably not less than about 2 wt %, and more preferably not less than about 3 wt %.

While the upper limit is not particularly limited, it is generally not more than about 70%, preferably not more than about 60 wt %, and more preferably not more than about 50 wt % in consideration of the viscosity of the composition and the like.

When practicing the present invention, the temperature is not particularly limited. To exhibit the reduced coenzyme $Q_{10}$-stabilizing effect to the maximum, the temperature is normally not more than 50° C., preferably not more than 40° C., more preferably not more than 30° C.

When processing into a dosage form for the oral administration mentioned below, moreover, the composition of the present invention is more preferably a liquid (including not only solution but also suspension, slurry or liposome) at ambient temperature or a temperature not less than the ambient temperature.

While the composition of the present invention can be used as it is, the composition can be processed into a dosage form for oral administration such as capsule (microcapsule, hard capsule, soft capsule), tablet, syrup, drink and the like and used preferably.

In addition, it can be processed into a dosage form for parenteral administration such as cream, suppository, toothpaste and the like and used preferably. Particularly preferred is a capsule, especially a soft capsule.

The capsule base material is not particularly limited, and gelatin derived from beef bones, cattle skin, pig skin, fish skin and the like, and other base materials (e.g., gum stabilizers) that can be used as food additives, such as seaweed-derived products (e.g., carageenan, alginic acid and the like), vegetable seed-derived products (e.g., locust bean gum, guar gum and the like), agents for production (e.g., celluloses) and the like) can also be used.

The stabilization method and production method of the present invention are preferable performed in combination under a deoxygenation atmosphere. That is, to exert the effect of the invention to the maximum extent, for example, the method of the present invention is preferably performed and the composition of the present invention is preferably prepared and/or preserved under a deoxygenation atmosphere such as inert gas atmosphere (e.g., nitrogen atmosphere etc.) and the like.

The above-mentioned processing and preservation after processing are also preferably performed under the above-mentioned deoxygenation atmosphere such as inert gas atmosphere and the like.

As mentioned above, by the co-presence of reduced coenzyme $Q_{10}$ and reduced coenzyme $Q_9$ and/or reduced coenzyme $Q_{11}$, the stability of reduced coenzyme $Q_{10}$ can be improved.

Reduced coenzyme $Q_9$ and reduced coenzyme $Q_{11}$ exhibit the same effect as provided by reduced coenzyme $Q_{10}$ in the body. Therefore, even when reduced coenzyme $Q_9$ and reduced coenzyme $Q_{11}$ contained in the reduced coenzyme $Q_{10}$ are ingested, they do not prevent the effect of the reduced coenzyme $Q_{10}$ but act in the same manner as the reduced coenzyme $Q_{10}$.

The present inventors have moreover studied intensively and found that the absorbability of reduced coenzyme $Q_9$ in the body is greater than that of the reduced coenzyme $Q_{10}$.

As mentioned above, since reduced coenzyme $Q_9$ and reduced coenzyme $Q_{10}$ act in the same manner in the body, a composition containing reduced coenzyme $Q_9$ and reduced coenzyme $Q_{10}$ in combination is expected to show higher absorption of coenzyme Q as a whole.

According to the present invention, reduced coenzyme $Q_{10}$ can be preferably protected from oxidation, and a composition free of an oxidation product of a reducing agent such as dehydroascorbic acids and the like can be provided optimally. Moreover, a composition showing high biological absorbability of reduced coenzyme $Q_{10}$ can also be provided.

EXAMPLES

The present invention is explained in more detail in the following by referring to Examples, which are not to be construed as limitative.

In Examples, the purity of reduced coenzyme $Q_{10}$, and the weight ratio of reduced coenzyme $Q_{10}$ and oxidized coenzyme $Q_{10}$ were determined by HPLC analysis as discussed below. However, the purity of the obtained reduced coenzyme $Q_{10}$ does not define the limit value of the purity in the present invention. Likewise, the proportion of reduced coenzyme $Q_{10}$ in the weight ratio of reduced coenzyme $Q_{10}$ and oxidized coenzyme $Q_{10}$ does not define the upper limit value thereof.

(HPLC Analysis Conditions)

column: SYMMETRY C18 (manufactured by Waters) 250 mm (length) 4.6 mm (inner diameter), mobile phase; $C_2H_5OH:CH_3OH=4:3$ (v:v), detection wavelength; 210 nm, flow rate; 1 ml/min, retention time of reduced coenzyme $Q_{10}$; 9.1 min, retention time of oxidized coenzyme $Q_{10}$; 13.3 min.

Production Example 1

Oxidized coenzyme $Q_{10}$ (100 g) and L-ascorbic acid (60 g) were added to 1000 g of ethanol, and the mixture was stirred at 78° C. to perform a reduction reaction. After 30 hr, the mixture was cooled to 50° C., and 400 g of ethanol was added while maintaining at the same temperature. The ethanol solution (containing 100 g of reduced coenzyme $Q_{10}$) was cooled to 2° C. at a cooling rate of 10° C./hr with stirring to give a white slurry. The obtained slurry was filtered under reduced pressure, the wet crystals were washed with cold ethanol, cold water and cold ethanol in this order (temperature of cold solvent used for washing, 2° C.) and dried under reduced pressure (20-40° C., 1-30 mmHg) to give white dry crystals (95 g). All operations except reduced-pressure drying were performed under a nitrogen atmosphere. The weight ratio of reduced coenzyme $Q_{10}$/oxidized coenzyme $Q_{10}$ of the obtained crystals was 99.4/0.6.

Production Example 2

Oxidized coenzyme $Q_9$ (10 g) and L-ascorbic acid (7 g) were added to 100 g of ethanol, and the mixture was stirred at 78° C. to perform a reduction reaction. After 30 hr, the mixture was cooled to 50° C., and ethanol (40 g), hexane (140 g) and water (140 g) were added in this order while maintaining at the same temperature. After removing the aqueous layer, the organic layer was concentrated under reduced pressure to give reduced coenzyme $Q_9$ as crystals.

Production Example 3

The reduced coenzyme $Q_{10}$ (9.85 g) obtained in Production Example 1 and reduced coenzyme $Q_9$ (0.15 g) obtained in Production Example 2 were mixed to give reduced coenzyme $Q_{10}$ containing 1.5 wt % of reduced coenzyme $Q_9$ (reduced coenzyme $Q_{10}$/oxidized coenzyme $Q_{10}$=99.4/0.6).

Production Example 4

Oxidized coenzyme $Q_{10}$ (10 g) containing 0.1% of oxidized coenzyme $Q_{11}$ and L-ascorbic acid (6 g) were added to 100 g of ethanol, and the mixture was stirred at 78° C. to perform a reduction reaction. After 30 hr, the mixture was cooled to 50° C., and 40 g of ethanol and water (10 g) were added while maintaining the same temperature. The ethanol solution (containing 10 g of reduced coenzyme $Q_{10}$) was cooled to 2° C. at a cooling rate of 10° C./hr with stirring to give a white slurry. The obtained slurry was filtered under reduced pressure, the wet crystals were washed with cold ethanol, cold water and cold ethanol in this order (temperature of cold solvent used for washing, 2° C.) and dried under reduced pressure (20-40° C., 1-30 mmHg) to give white dry crystals (9.5 g). All operations except reduced-pressure drying were performed under a nitrogen atmosphere. The obtained crystals contained 0.1% of reduced coenzyme $Q_{11}$ and the weight ratio of reduced coenzyme $Q_{10}$/oxidized coenzyme $Q_{10}$ of the obtained crystals was 99.4/0.6.

Example 1

The reduced coenzyme $Q_{10}$ (reduced coenzyme $Q_{10}$/oxidized coenzyme $Q_{10}$=99.4/0.6) containing 1.5 wt % of reduced coenzyme $Q_9$ obtained in Production Example 3 and crystals of reduced coenzyme $Q_{10}$ (reduced coenzyme $Q_{10}$/oxidized coenzyme $Q_{10}$=99.4/0.6) free of reduced coenzyme $Q_9$, which were obtained in Production Example 1, were maintained in a condition exposed to air at 25° C. The results of reduced coenzyme $Q_{10}$/oxidized coenzyme $Q_{10}$ ratio after the lapse of 24 hr are shown in Table 1.

TABLE 1

| | weight ratio of reduced coenzyme $Q_{10}$/oxidized coenzyme $Q_{10}$ |
|---|---|
| reduced coenzyme $Q_{10}$ containing 1.5% of reduced coenzyme $Q_9$ | 96.7/3.3 |
| reduced coenzyme $Q_{10}$ free of reduced coenzyme $Q_9$ | 95.5/4.5 |

Example 2

50 mg of the reduced coenzyme $Q_{10}$ (reduced coenzyme $Q_{10}$/oxidized coenzyme $Q_{10}$=99.4/0.6) containing 1.5 wt % of reduced coenzyme $Q_9$ obtained in Production Example 3 or 50 mg of reduced coenzyme $Q_{10}$ (reduced coenzyme $Q_{10}$/oxidized coenzyme $Q_{10}$=99.4/06) free of reduced coenzyme $Q_9$, which were obtained in Production Example 1, was added to 5 g of ethanol and stirred in the air at 25° C. The resulting reduced coenzyme $Q_{10}$/oxidized coenzyme $Q_{10}$ ratio after stirring for 6 hr are shown in Table 2.

TABLE 2

| | weight ratio of reduced coenzyme $Q_{10}$/oxidized coenzyme $Q_{10}$ |
|---|---|
| reduced coenzyme $Q_{10}$ containing 1.5% of reduced coenzyme $Q_9$ | 90.2/9.8 |
| reduced coenzyme $Q_{10}$ free of reduced coenzyme $Q_9$ | 87.2/12.8 |

Example 3

Crj:CD (SD) rats (5-week-old, 15 males, 15 females, body weight 260 g-300 g) were divided into 3 groups (5 per group) for each of male and female. A first group was used as a control group, and corn oil (3 ml/kg) was orally administered once a day for 14 days. A second group was orally administered a corn oil solution of the reduced coenzyme $Q_9$ obtained in Production Example 2, which was prepared to meet the dose of reduced coenzyme $Q_9$ of 600 mg/kg, once a day for 14 days at a dose of 3 ml/kg. A third group was orally administered a corn oil solution of reduced coenzyme $Q_{10}$ obtained in Production Example 1, which was prepared to meet the dose of reduced coenzyme $Q_{10}$ of 600 mg/kg, once a day for 14 days at a dose of 3 ml/kg. At 24 hr after the final administration, blood samples were collected to give plasma samples. Using HPLC, the concentration of coenzyme Q in the obtained plasma was measured. The results are shown in the bar graph of FIG. 1.

In FIG. 1, the vertical axis shows the concentration of total coenzyme Q in the plasma, and each bar shows the average±standard deviation. As is clear from FIG. 1, in both male and female, the concentration of total coenzyme Q in the plasma increased in the reduced coenzyme $Q_9$ administration group as compared to the reduced coenzyme $Q_{10}$ administration group.

Preparation Example

To a mixture of canola oil, diglycerol monooleate (Poem DO-100 V manufactured by Riken Vitamin), hydrogenated oil, bees wax and lecithin were added crystals of reduced coenzyme $Q_{10}$ containing 0.6 wt % of oxidized coenzyme $Q_{10}$ and 0.1 wt % of reduced coenzyme $Q_{11}$, and a soft capsule of gelatin containing 30 mg of reduced coenzyme $Q_{10}$ and having the following formulation was prepared by a conventional method.

| | |
|---|---|
| reduced coenzyme $Q_{10}$ | 10.0 wt % |
| diglycerolmonooleate | 32.0 wt % |
| canola oil | 33.0 wt % |
| hydrogenated oil | 17.0 wt % |
| bees wax | 6.0 wt % |
| lecithin | 2.0 wt % |

Example 4

Oral Absorbability Test

Figure 2:
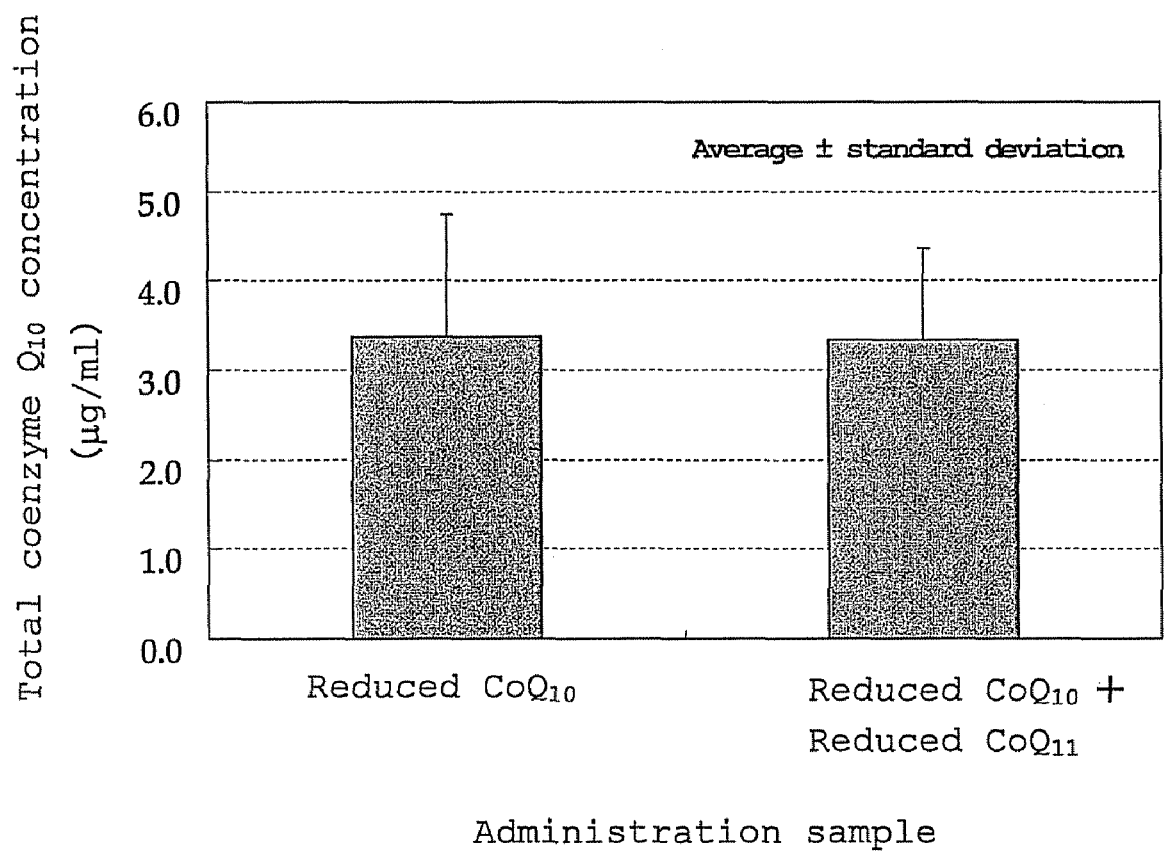
FIG. 2 is a bar graph that sets forth the concentration of the total coenzyme Q (µg/ml) in plasma from male rats following the administration of (1) reduced coenzyme $Q_{10}$ or (2) a reduced coenzyme $Q_{10}$ and reduced coenzyme $Q_{11}$ mixture as set forth in Example 4.

Crj:CD (SD) rats (about 77-week-old, 10 male rats) were prepared. Reduced coenzyme $Q_{10}$ was orally administered to 5 of them, and a mixture of reduced coenzyme $Q_{10}$ and reduced coenzyme $Q_{11}$ (containing 0.1% of reduced coenzyme $Q_{11}$) was orally administered to the remaining 5 of them, each as a 25 mg/ml soy bean oil solution at a dose of 4.0 ml/kg. At 2 hr from the administration, blood was drawn and centrifuged to give plasma samples. Using HPLC, the concentration of coenzyme $Q_{10}$ in the obtained plasma was measured. The results are shown in the bar graph of FIG. 2. As is clear from FIG. 2, the concentration of coenzyme $Q_{10}$ in the plasma was about 3.4 µg/ml resulting from the administration of both reduced coenzyme $Q_{10}$ and a mixture of reduced coenzyme $Q_{10}$ and reduced coenzyme $Q_{11}$.

While some of the embodiments of the present invention have been described in detail above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

This application is based on application No. 2006-126897 filed in Japan, the contents of which are incorporated hereinto by reference.

The invention claimed is:

1. A method for stabilizing reduced coenzyme $Q_{10}$, which method comprises preparing a reduced coenzyme $Q_{10}$-containing composition comprising reduced coenzyme $Q_{10}$ and one or both of (a) and (b):
   (a) not less than 1.5 wt % to not more than 99 wt % of reduced coenzyme $Q_9$ relative to reduced coenzyme $Q_{10}$, and
   (b) reduced coenzyme $Q_{11}$,
   wherein not less than 0.01 wt % of reduced coenzyme $Q_{10}$ is contained in the composition, and
   wherein the proportion of reduced coenzyme $Q_{10}$ relative to the total amount of coenzyme $Q_{10}$ is not less than 90 wt %,
   thereby stabilizing reduced coenzyme $Q_{10}$.

2. The method of claim 1, wherein the method comprises preparing one or both of (a) the reduced coenzyme $Q_9$ and (b) the reduced coenzyme $Q_{11}$, and then
   adding one or both of (a) the reduced coenzyme $Q_9$ and (b) the reduced coenzyme $Q_{11}$ to the reduced coenzyme $Q_{10}$ to prepare the reduced coenzyme $Q_{10}$-containing composition.

3. The method of claim 1, wherein the method comprises providing a composition comprising oxidized coenzyme $Q_{10}$ with one or both of oxidized coenzyme $Q_9$ and oxidized coenzyme $Q_{11}$, and then
   reducing oxidized coenzyme $Q_{10}$ and reducing one or both of oxidized coenzyme $Q_9$ and oxidized coenzyme $Q_{11}$ to prepare the reduced coenzyme $Q_{10}$-containing composition.

4. The method of claim 1, wherein the reduced coenzyme $Q_{10}$-containing composition is prepared under a deoxygenation atmosphere.

5. A reduced coenzyme $Q_{10}$-containing composition comprising reduced coenzyme $Q_{10}$ and one or both of (a) and (b):
   (a) not less than 1.5 wt % to not more than 99 wt % of reduced coenzyme $Q_9$ relative to reduced coenzyme $Q_{10}$, and
   (b) reduced coenzyme $Q_{11}$
   wherein not less than 0.01 wt % of reduced coenzyme $Q_{10}$ is contained in the composition, and
   wherein the proportion of reduced coenzyme $Q_{10}$ relative to the total amount of coenzyme $Q_{10}$ is not less than 90 wt %.

6. The composition of claim 5, wherein the reduced coenzyme $Q_{10}$ is in crystalline form.

7. The composition of claim 5, wherein the reduced coenzyme $Q_{10}$ is dissolved or suspended in a solvent.

8. The composition of claim 5, wherein the reduced coenzyme $Q_{10}$ is a melt.

9. The composition of claim 5, which further comprises a pharmaceutically acceptable carrier.

10. The composition of claim 5, which is in a form suitable for administration to a mammal and comprises reduced coenzyme $Q_{10}$ as an active ingredient.

11. The composition of claim 5, which further comprises at least one component selected from the group consisting of an excipient, a disintegrant, a lubricant, a binder, an antioxidant, a coloring agent, an anticoagulant, an absorption promoter, a solubilizing agent for the active ingredient, a stabilizer, an active ingredient other than reduced coenzyme $Q_{10}$, and combinations thereof.

12. An oral dosage form comprising the composition of claim 11, which dosage form is a capsule.

13. The oral dosage form of claim 12, wherein the capsule is a microcapsule, a soft capsule, or a hard capsule.

14. A method for producing a reduced coenzyme $Q_{10}$-containing composition, which method comprises
   preparing one or both of (a) reduced coenzyme $Q_9$ and (b) reduced coenzyme $Q_{11}$, and then
   adding one or both of (a) the reduced coenzyme $Q_9$ and (b) the reduced coenzyme $Q_{11}$ to reduced coenzyme $Q_{10}$ to prepare the reduced coenzyme $Q_{10}$-containing composition,
   wherein the composition comprises reduced coenzyme $Q_{10}$ and one or both of (a) not less than 1.5 wt % to not more than 99 wt % of reduced coenzyme $Q_9$ relative to reduced coenzyme $Q_{10}$ and (b) reduced coenzyme $Q_{11}$,
   wherein not less than 0.01 wt % of reduced coenzyme $Q_{10}$ is contained in the composition, and
   wherein the proportion of reduced coenzyme $Q_{10}$ relative to the total amount of coenzyme $Q_{10}$ is not less than 90 wt %.

15. A method for producing a reduced coenzyme $Q_{10}$-containing composition, which method comprises
   providing a composition comprising oxidized coenzyme $Q_{10}$ with one or both of oxidized coenzyme $Q_9$ and oxidized coenzyme $Q_{11}$, and then
   reducing oxidized coenzyme $Q_{10}$ and reducing one or both of oxidized coenzyme $Q_9$ and oxidized coenzyme $Q_{11}$ to prepare the reduced coenzyme $Q_{10}$-containing composition,
   wherein the composition comprises reduced coenzyme $Q_{10}$ and one or both of (a) not less than 1.5 wt % to not more than 99 wt % of reduced coenzyme $Q_9$ relative to reduced coenzyme $Q_{10}$ and (b) reduced coenzyme $Q_{11}$,
   wherein not less than 0.01 wt % of reduced coenzyme $Q_{10}$ is contained in the composition, and
   wherein the proportion of reduced coenzyme $Q_{10}$ relative to the total amount of coenzyme $Q_{10}$ is not less than 90 wt %.

16. The composition of claim 5, wherein the reduced coenzyme $Q_{10}$-containing composition comprises not less than 1.5 wt % to not more than 99 wt % of reduced coenzyme $Q_9$ relative to reduced coenzyme $Q_{10}$.

17. The composition of claim 5, wherein the reduced coenzyme $Q_{10}$-containing composition comprises reduced coenzyme $Q_{11}$.

18. The composition of claim 5, wherein the reduced coenzyme $Q_{10}$-containing composition comprises not less than 96 wt % of reduced coenzyme $Q_{10}$ relative to the total amount of coenzyme $Q_{10}$.

* * * * *